United States Patent [19]

Schwartz et al.

[11] 4,442,128

[45] Apr. 10, 1984

[54] PRODUCTION OF FERMENTED WHEY PRODUCTS CONTAINING A THICKENING POLYMER

[75] Inventors: Robert D. Schwartz, Concord; Elizabeth A. Bodie, El Cerrito, both of Calif.

[73] Assignee: Stauffer Chemical Company, Westport, Conn.

[21] Appl. No.: 284,421

[22] Filed: Jul. 20, 1981

[51] Int. Cl.³ ...................... A23C 21/02; C12P 19/06; C12N 1/14; C12R 1/64
[52] U.S. Cl. ........................................ 426/41; 426/43; 435/104; 435/253; 435/910
[58] Field of Search ............... 435/104, 245, 253, 910; 426/41, 43

[56] References Cited

U.S. PATENT DOCUMENTS 3,343,962  9/1967  Peer .................................. 435/253 X
3,455,786  7/1969  Miescher ......................... 435/910 X
3,497,359  2/1970  Peer .................................. 435/41 X

OTHER PUBLICATIONS

Stauffer et al., Extracellular Microbial Polysaccharide Production by Fermentation on Whey or Hydrolyzed Whey, Journal of Food Science, vol. 43, 1978 (pp. 756–758).
Manual for Dairy Manufacturing Short Courses, Within U.S.A., Kurtz Bros., Clearfield, Pa., 1956, (pp. 56–57).

Primary Examiner—David M. Nafe
Attorney, Agent, or Firm—Michael J. Bradley

[57] ABSTRACT

Dairy whey, a waste product of chesse production, is fermented with an organism to produce a whey product containing a thickening polymer that serves as a thickening agent. Fermentation is carried out by forming a fermentation broth of whey and glucose, and optionally a water soluble phosphate and/or yeast extract and then fermenting the broth with *Xanthomonas campestris* ATCC 31922. The resultant fermented whey product is used as a thickening agent in the food industry.

10 Claims, 3 Drawing Figures

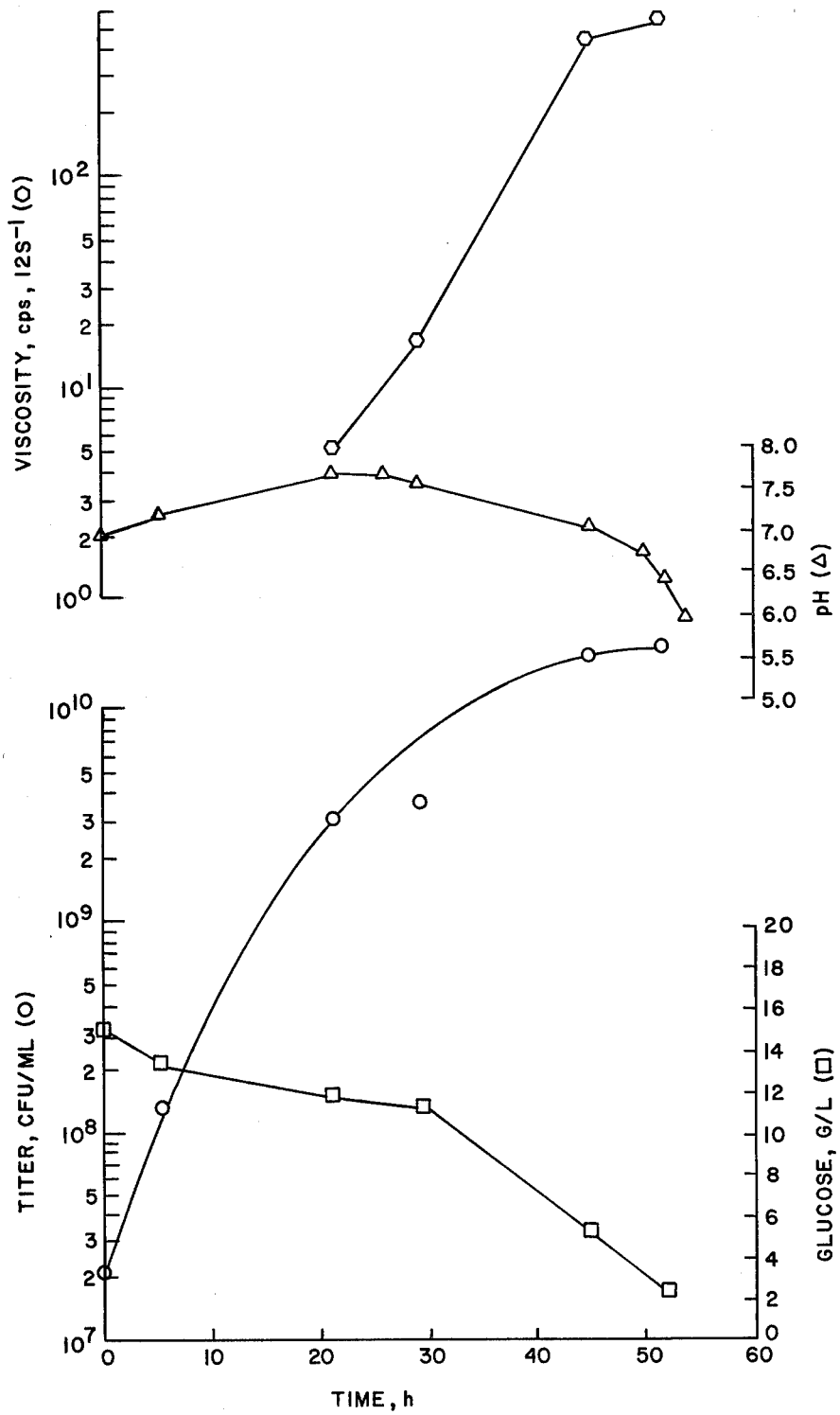
FIGURE I
X. CAMPESTRIS ATCC-31922 FERMENTATION IN WHEY-GLUCOSE MEDIUM

FIGURE II
VISCOSITY VS. SHEAR RATE CURVE FOR DRIED FUNCTIONALIZED WHEY
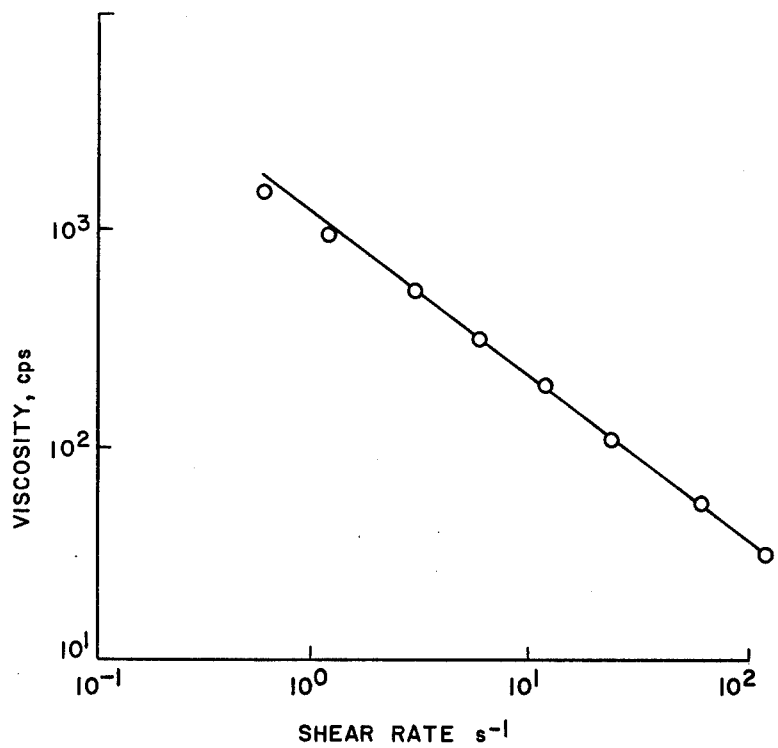

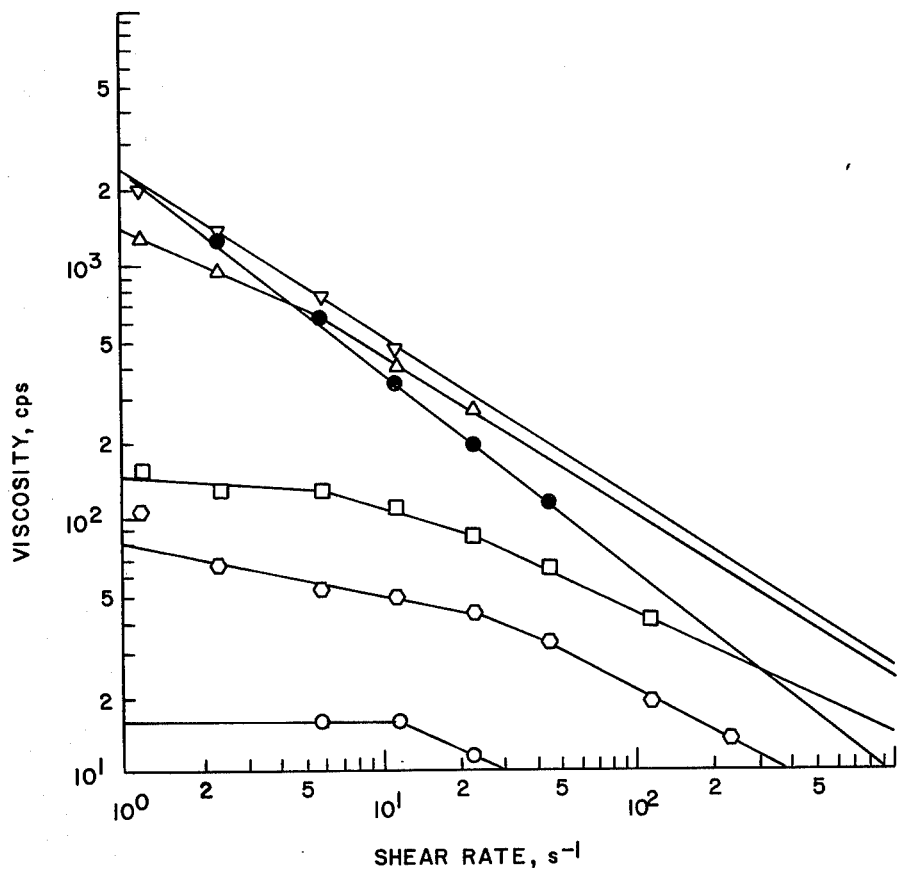
FIGURE III
VISCOSITY VS. SHEAR RATE OF FUNCTIONALIZED WHEY
● RECONSTITUTED BROTH (2% TEKLAC + 0.4% KELTROL)
△ 1% TEKLAK + 1% GLUCOSE
▽ 0.5% TEKLAK + 1.5% GLUCOSE
○ 0% TEKLAK + 2% GLUCOSE
○ 2% TEKLAK
□ GLUCOSE MINIMAL (1.5% GLU + 0.5% $K_2HPO_4$ + 0.2% $NH_4Cl$ + 0.1% NaCl + 0.01% $MgSO_4$ + 0.1% YE

PRODUCTION OF FERMENTED WHEY PRODUCTS CONTAINING A THICKENING POLYMER

BRIEF DESCRIPTION OF THE INVENTION

The process of this invention provides a method of functionalizing whey by forming a fermentation broth of the whey, glucose and optionally water-soluble phosphate as a pH buffer, and yeast extract and then fermenting this whey broth with the novel organism *Xanthomonas campetris* strain BB-1 (ATCC 31922) on deposit with the American Type Culture Collection, Rockville, Md.

BACKGROUND OF THE INVENTION

Controlled fermentation of food can be used as a means of improving functionality of food. Dairy whey, a food, may be an economical source of a fermentable substrate, and is widely used as an accepted milk-derived ingredient in manufactured foods. If whey can be functionalized by fermentation with an organism that produces a thickening polymer when grown on the whey substrate, it is possible to obtain whey products that may serve the function of a stabilizer, thickener, emulsifier, or flavor enhancer.

Whey is the fluid medium containing a very low concentration of milk solids and a high concentration of lactose. Disposal of this waste by-product by drying is an energy-intensive, expensive procedure which results in an expensive by-product. Sewering of the whey is prohibitive in cost due to the high biological oxygen demand which is placed on municipal sewer systems.

The most desirable method of handling a whey waste stream is to produce a high quality natural food ingredient from the whey waste product. Applicant has discovered a novel method of producing a functionalized whey product for use as a food ingredient or any type of product where milk solids and lactose are acceptable ingredients.

DESCRIPTION OF THE DRAWINGS

FIG. I shows a graph of a fermentation of *Xanthomonas campestris* ATCC 31922 in a medium containing 2% Teklac (whey), 1.5% glucose, and 0.025% yeast extract.

FIG. II shows a viscosity versus shear rate curve for a typical dried functionalized whey produced by the fermentation techniques of this invention.

FIG. III shows a graph of viscosity vs. shear rate after 128 hours fermentation with *X. campestris* ATCC 31922 in the following media: 2% Teklac, 0.25% $K_2HPO_4$, 0.01% yeast extract; 1% Teklac, 1% glucose, 0.25% $K_2HPO_4$, 0.01% yeast extract; 0.5% Teklac, 1.5% glucose, 0.25% $K_2HPO_4$, 0.01% yeast extract; 2% glucose, 0.25% $K_2HPO_4$, 0.01% yeast extract; 1.5% glucose, 0.5% $K_2HPO_4$, 0.2% $NH_4Cl$, 0.1% NaCl, 0.01% $MgSO_4$, 0.1% yeast extract. Also shown is a curve for a reconstituted broth (not fermented) containing 2% teklac, 0.4% Keltrol® (food grade xanthan gum sold by Kelco, Inc., San Diego, CA).

DETAILED DESCRIPTION OF THE INVENTION

A functionalized dairy whey product having a viscosity greater than 200 centipoise at a $12s^{-1}$ shear rate for use as a food ingredient that may serve as a stabilizer, thickener, or emulsifier, can be produced by fermenting a mixture comprising whey, glucose, optionally yeast extract and a pH buffer with the organism *Xanthomonas campestris* ATCC 31922 to produce a functionalized whey product containing a thickening polymer produced by the novel organism *Xanthomonas campestris* ATCC 31922.

Derivation of *Xanthomonas campestris* ATCC

*X. campestris* ATCC 31922 was isolated for its ability to grow in whey. It was derived from *X. campestris* NRRL B-1459 following several serial passages in Teklac (whey) medium containing 2% Teklac, 0.25% $K_2HPO_4$, 0.01% yeast extract. In this medium, at about 28° C., BB-1 has a generation time of about two hours, viable cell titers of about $10^9/1$ or greater are reached, the lactose in the medium is not metabolized, and the broth does not become viscous.

Although it is known in the art that an ultra-filtered and hydrolyzed whey medium fermented with *Xanthomonas campestris* results in excellent polymer formation, all growth to date on unhydrolyzed whey has failed to result in polymer production: see K. R. Stauffer and J. G. Leeder, 1978, *J. Food Sci.*, 43: 756–758, "Extracellular Microbial Polysaccharide Production by Fermentation on Whey or Hyrolyzed Whey," and M. Charles and M. K. Radjai, 1977 "Xanthan Gum From Acid Whey" in *Extracullular Microbial Polysaccharides*, eds. P. A. Sandford and A. I. Laskin. ACS Symp. Ser. No. 45, pp. 27–39. Fermentation of a whey broth comprising unhdryrolyzed whey (acid or sweet), glucose, and optionally yeast extract and phosphate results in polymer formation and functionalization of the whey so that the whey product can be utilized as a food ingredient. This aerobic fermentation can be carried out preferably in a pH range of 6 to 8, preferably with the pH maintained in a range from about 6.5 to about 7.5. The fermentation can be carried out at a temperature from about 20° to 35° C., preferably carried out at a temperature from about 25° to about 30° C. Typical composition of Teklac (sweet dairy whey) is as follows:

| CHEMICAL AND PHYSICAL SPECIFICATIONS Ingredient Listing: Whey | |
|---|---|
| Typical Proximate Analysis | |
| Protein (N × 6.38) % | 12.7 |
| Fat % | 1.1 (1.25% Maximum) |
| Moisture % | 4.5 (5.0% Maximum) |
| Ash % | 8.0 |
| Lactose % | 71.3 |
| Calories, Cal/100 g | 350.0 |
| Typical Vitamin & Mineral Analysis | |
| Vitamin A I.U./100 g | Nil |
| Vitamin C mg/100 g | Nil |
| Thiamin mg/100 g | 0.40 |
| Riboflavin mg/100 g | 1.76 |
| Niacin mg/100 g | 1.00 |
| Calcium % | 0.71 |
| Iron % | Nil |
| Vitamin $B_{12}$ µg/100 g | 2.12 |
| Phosphorus % | 0.69 |
| Pantothenic Acid mg/100 g | 4.09 |
| Microbiological Standards | |
| Standard Plate Count | 10,000/g (Maximum) |
| Coliforms | 9/g (Maximum) |
| *E. coli* | Negative |
| Salmonella | Negative |

The nutritional values listed above are within 80% of the value declared in compliance with Federal Nutritional Regulations 21 CFR §1.17(4)(ii).

|  | Typical Range | Limit |
|---|---|---|
| Solubility Index | 0.1–0.5 ml | 1.25 ml Max. |
| Acidity | 0.10–0.14% | 0.16 Max. |
| Alkalinity of Ash | 175–200 ml | 225 ml Max. |
| Scorched Particles | 7.5 mg | 15.0 mg Max. |
| Particle size (Through 40 Mesh) | 99–100% | 98% Min. |

Concentration of whey can range from about 0.5% to about 12.0%, preferably from about 1% to about 3%, and the concentration of added glucose can range from about 0.5% to about 12.0%, preferably 1% to 3%. The additional yeast extract in the fermentation broth can range from about 0 to about 0.5%, preferably from about 0.01% to about 0.025%. Concentration of optional phosphate can range from 0 to about 0.25% $K_2HPO_4$ as desired. Adequate fermentation broth viscosities (>200 cps and preferably >800 cps at a 12 $s^{-1}$ shear rate) are usually reached with 30 to 50 hours. All of the above weight percents are in weight per volume.

EXAMPLE 1

FIG. I shows a typical fermentation of a whey-glucose broth medium containing 2% Teklac, 1.5% glucose, and 0.025% yeast extract that has been fermented with *Xanthomonas campestris* ATCC 31922. The medium was sterilized by autoclave for 20 minutes. The fermentation was conducted in a fermentor to which air was pumped at the rate of one 1/1/min, agitation was at the rate of 800 rmp, the dissolved oxygen concentration maintained at 70 to 90% saturation, and the temperature was 28° C. A Bio-flow ® fermentor was used (New Brunswick Scientific Co., N.J.). The initial pH was 7 and was not controlled. The figure shows the general increase in viscosity over time, an 86–87% decrease in glucose concentration, growth of the organism, and the initial increase in pH, followed by a decrease in pH, typical of this fermentation.

EXAMPLE 2

The functionalized whey was produced by *Xanthomonas campestris* ATCC 31922 in a New Brunswick Scientific Co., 14 l Microferm fermentor containing about 10 l medium on a fermentation medium comprising 2% Teklac, 3% glucose, 0.25% $K_2HPO_4$, and 0.1 yeast extract. The inoculum was grown about 200 hours in the same medium without glucose. The viable cell titer at the time of use was $9 \times 10^8$/ml. Fermentation conditions were as follows: Temperature—28° C.; Agitation—550 rpm; Aeration—one 1/1/min.; pH—6.8 initially, not controlled; Approximately 2 ml of Antifoam P 2000 (Dow Chemical Co.) added at start of fermentation Table I shows fermentation time, the amount of glucose in grams per liter and viscosity of the sequential samples of the fermentation broth taken at the times indicated. The fermentation broth was then autoclaved at 15 psi for 20 minutes.

TABLE I

| Time, H | Glucose G/L | Viscosity @ 12S$^{-1}$ 1:5 Dilution |
|---|---|---|
| 0 | 31.9 | ND |
| 44 | 13.5 | 134 (675) |
| 71 | ND | ND |
| 115 | 12.9 | 149 (745) |
| Post-autoclave | 12.7 | 216 (1080) |

ND, not determined
( ) Back calculated viscosity, i.e.: 5 (134) = 675.

The lactose in the fermentation broth is not utilized for either growth of the organism *Xanthomonas campestris* ATCC 31922 or production of polymer.

EXAMPLE 3

The fermentation conditions in the fermentation in Example 1 were modified as follows: The fermentor medium was simplified to contai 2% Teklac, 2% glucose, 0.025% yeast extract, (i.e., no $K_2HPO_4$, reduced glucose and yeast extract); pH controlled so as not to rise above 7.5 using phosphoric acid addition. The fermentation was conducted for 94 hours. Table II shows results of four such fermentations and the resulting characteristics of the combined sample of fermentations 1, 2, 3, and 4, following autoclaving. As shown, 77–97% of the glucose was consumed, the lactose was not metabolized, and the viscosity increased after autoclaving.

TABLE II

Functionalized whey production by *X. campestris* ATCC 31922 in 14 l fermentors.

|  | Fermentor | | | |
|---|---|---|---|---|
|  | 1 | 2 | 3 | 4 |
| Before Autoclaving | | | | |
| viscosity, cps @ 12 s$^{-1}$ | 440 | 502 | 564 | 556 |
| pH | 5.35 | 5.61 | 5.12 | 5.30 |
| glucose, g/l | 0.57 | 4.68 | 3.23 | 3.41 |
| lactose, g/l | 12.59 | 15.17 | 14.09 | 15.55 |
| color | yellow-white | yellow-white | yellow-white | yellow-white |
| After Autoclaving combined sample | | | | |
| viscosity, cps @ 12 s$^{-1}$ | 766 | | | |
| pH | 5.36 | | | |
| glucose, g/l | 2.71 | | | |
| lactose, g/l | 15.01 | | | |
| color | yellow-white | | | |
| dry weight, g/l | 28.7 | | | |

The high viscosity broths produced by fermentation techniques of this invention may be dried and/or sterilized by autoclave and lyophilization, spray drying, or other techniques.

EXAMPLE 4

A viscosity versus shear rate curve for a typical dried functionalized whey so produced is shown in FIG. II. The sample was tested on a 2.5 XLVT Wells-Brookfield microviscometer having a 3° cone at 25° C. The sample size was 2.0 milliliters. The sample consisted of a 1% solution (weight/vol) of functionalized whey in deionized water. The pH was 5.8, glucose concentration was 0.9 grams per liter, and lactose concentration was 4.3 grams per liter. The increase in viscosity with decrease in shear rate is typical of pseudoplastic polymers.

EXAMPLE 5

FIG. III shows a graph of viscosity vs. shear rate after 128 hours fermentation with *X. campestris* ATCC 31922 in the following media: 2% Teklac, 0.25% $K_2HPO_4$, 0.01% yeast extract; 1% Teklac, 1% glucose, 0.25% $K_2HPO_4$, and 0.01% yeast extract; 0.5% Teklac, 1.5% glucose, 0.25% $K_2HPO_4$, 0.01% yeast extract; 2% glucose, 0.25% $K_2HPO_4$, 0.01% yeast extract; 1.5% glucose, 0.5% $K_2HPO_4$, 0.2% $NH_4Cl$, 0.1% NaCl, 0.01% $MgSO_4$, 0.1% yeast extract. Also shown is a curve for a reconstituted broth (not fermented) containing 2% Teklac, 0.5% Keltrol® (food grade xanthan gum sold by Kelco, Inc., San Diego, CA).

At the lowest shear rates, the viscosity observed in fermented broths containing both Teklac and glucose is at least ten times greater than that observed in the presence of Teklac or glucose alone. Further, the high viscosity fermented broths behave the same as a reconstituted broth containing xanthan gum at a concentration making it suitable for use in the food industry, i.e., useful in ice cream.

The functionalized whey product of this invention can be used as a food ingredient where milk solids and/or whey, and/or thickeners, and/or stabilizers are used such as in ice cream, salad dressing, foam stabilizer (meringue), puddings, snack foods, etc.

What is claimed is:

1. A process for producing a functionalized dairy whey product comprising the steps of:
   (a) forming a fermentation broth of unhydrolyzed whey containing unhydrolyzed lactose, and glucose; and
   (b) fermenting the broth with the organism *Xanthomonas campestris* ATCC 31922 to produce a functionalized dairy whey product containing a thickening polymer produced by the organism.

2. The process of claim 1 wherein the concentration of the whey is from about 0.5% to about 12% weight per volume and the glucose is from about 0.5% to about 12% weight per volume.

3. The process of claim 1 wherein an additional ingredient of the fermentation broth is yeast extract.

4. The process of claim 1 wherein an additional ingredient of the fermentation broth is up to about 0.5% weight per volume of yeast extract.

5. The process of claim 1 wherein an additional ingredient of the fermentation broth is $K_2HPO_4$.

6. The process of claim 1 wherein an additional ingredient of the fermentation broth is up to about 0.25% weight per volume $K_2HPO_4$.

7. The process of claim 1 wherein the fermentation is conducted at a temperature of from about 20° to about 35° C.

8. The process of claim 1 wherein the fermentation is conducted at a temperature of from about 20° to about 35° C. and the pH is maintained in a range of from about 6 to about 8.

9. The process of claim 1 plus the additional step:
   (c) drying said functionalized whey product to form a dry functionalized whey product.

10. A biologically pure culture of the organism *Xanthomonas compestris* ATCC 31922 having the ability to grow in a fermentation broth of unhydrolyzed whey containing unhydrolyzed lactose and glucose to produce a functionalized whey product containing a thickening polymer produced by the organism.

* * * * *